US006925334B1

(12) United States Patent
Salys

(10) Patent No.: US 6,925,334 B1
(45) Date of Patent: Aug. 2, 2005

(54) IMPLANTABLE MEDICAL LEAD HAVING MULTIPLE, JOINTLY INSULATED ELECTRICAL CONDUCTORS

(75) Inventor: Scott Salys, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 11 days.

(21) Appl. No.: 10/634,580

(22) Filed: Aug. 4, 2003

(51) Int. Cl.[7] .............................................. A61N 1/05
(52) U.S. Cl. ...................... 607/116; 607/119; 607/122; 600/374
(58) Field of Search ................................ 600/374, 375, 600/372, 381, 394; 607/116, 119, 122, 126, 607/127–131

(56) References Cited

U.S. PATENT DOCUMENTS

| | | | |
|---|---|---|---|
| 3,348,548 A * | 10/1967 | Chardack ..................... | 607/122 |
| 4,497,849 A | 2/1985 | Hughes et al. .............. | 427/120 |
| 4,559,951 A * | 12/1985 | Dahl et al. .................. | 600/374 |
| 5,016,646 A | 5/1991 | Gotthardt et al. ........... | 128/784 |
| 5,156,151 A * | 10/1992 | Imran .......................... | 600/375 |
| 5,358,517 A * | 10/1994 | Pohndorf et al. ............ | 607/116 |
| 5,391,147 A * | 2/1995 | Imran et al. ................. | 604/528 |
| 5,425,755 A | 6/1995 | Doan ............................ | 607/119 |
| 5,449,381 A * | 9/1995 | Imran .......................... | 607/122 |
| 5,769,077 A * | 6/1998 | Lindegren .................... | 600/373 |
| 5,796,044 A * | 8/1998 | Cobian et al. ............... | 174/103 |
| 5,893,885 A * | 4/1999 | Webster, Jr. ................. | 607/122 |
| 5,935,159 A * | 8/1999 | Cross et al. ................. | 607/116 |
| 6,321,102 B1 * | 11/2001 | Spehr et al. ................. | 600/374 |
| 6,324,415 B1 | 11/2001 | Spehr et al. ................. | 600/374 |
| 6,587,733 B1 * | 7/2003 | Cross et al. ................. | 607/116 |
| 6,785,576 B2 * | 8/2004 | Verness ....................... | 607/122 |

FOREIGN PATENT DOCUMENTS

WO    WO 98/29055    7/1998

* cited by examiner

Primary Examiner—Jeffrey R. Jastrzab

(57) ABSTRACT

An implantable lead for transmitting electrical signals between a proximal end and a distal end comprises an elongated lead body defining a longitudinally-extending lumen, and a plurality of individual electrical conductors contained in the lumen of the lead body and extending between the proximal and distal ends, the plurality of individual conductors sharing a common insulating coating. Each of the plurality of individual electrical conductors preferably comprises a braided, multifilar cable conductor. In one embodiment, the common insulating coating electrically isolates the plurality of conductors from each other, and may include a bridging portion extending between individual conductors.

The plurality of electrical conductors and the common insulating coating comprise a conductor assembly that may have a helical configuration defining a longitudinally-extending passageway for receiving a stylet, guide wire, or the like, for placement of the distal end of the lead. Alternatively, the conductor assembly may have a tubular configuration, the plurality of individual conductors being embedded therein in spaced-apart, parallel relationship or along a generally helical path along the length of the lead body for greater lead flexibility.

6 Claims, 2 Drawing Sheets

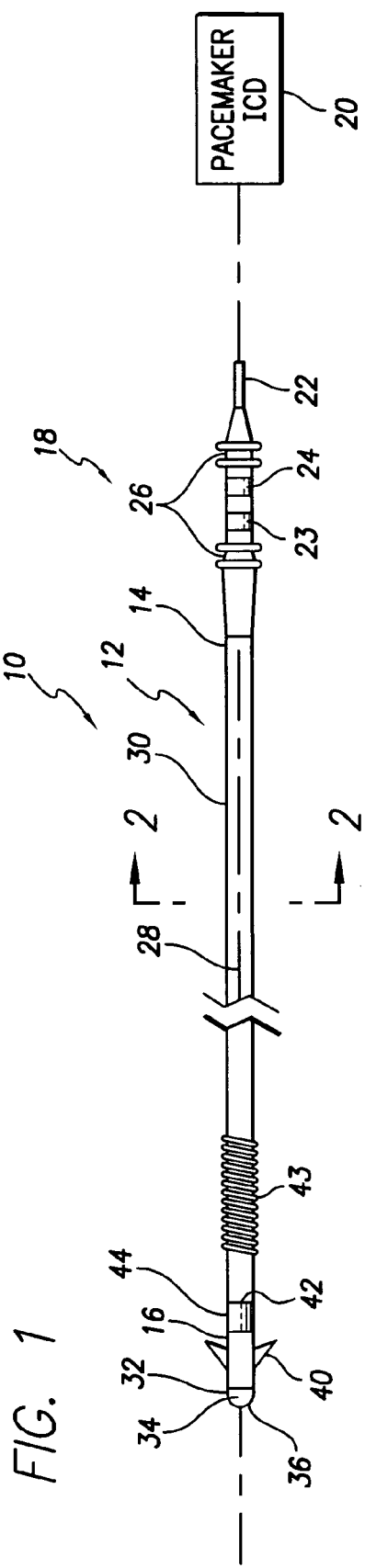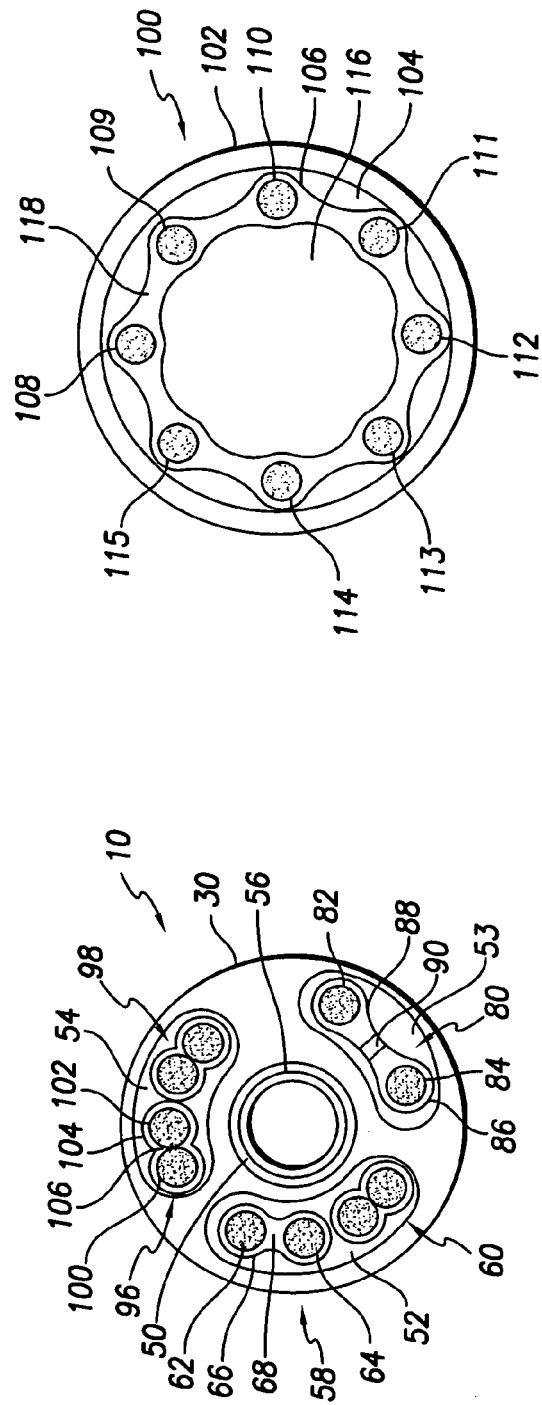

IMPLANTABLE MEDICAL LEAD HAVING MULTIPLE, JOINTLY INSULATED ELECTRICAL CONDUCTORS

FIELD OF THE INVENTION

The present invention relates generally to implantable medical leads and particularly to reduced diameter implantable leads employing multiple electrical conductors.

BACKGROUND OF THE INVENTION

Many of today's intravascular endocardial leads are multipolar leads typically comprising a tip electrode and one or more ring electrodes disposed along the distal end of the lead body. The various electrodes transmit electrical stimulation pulses from an implantable medical device such as a pacemaker or implantable cardioverter defibrillator (ICD) to the tissue to be stimulated, and/or transmit naturally occurring sensed electrical signals from the tissue to the medical device. In a typical bipolar lead having a tip electrode and a ring electrode, two helically wound conductor coils with insulation in between are arranged coaxially and carried within a single lumen of the lead body. The inner conductor coil connects the medical device with the tip electrode while the outer conductor coil, somewhat shorter than the inner coil, connects the medical device with the ring electrode positioned proximally of the tip electrode.

To accommodate placement of multipolar leads into the coronary veins or permit their use with other leads (such as in four-chamber or whole heart pacing) it has become necessary to reduce the outside diameter of the leads. In one approach to accomplishing this goal, the various conductor coils, each individually insulated, are interleaved and wound about the same coil diameter instead of being arranged coaxially.

To further reduce the outside diameter of multipolar leads, lead bodies having multiple lumens have been developed. In place of helically wound coils, individually insulated, monofilament, non-coiled wire conductors or multifilar, braided cable conductors are used to connect the medical device with the electrodes along the distal end of the lead. Multilumen lead bodies may also carry defibrillation electrodes supplied by associated cable or wire conductors.

In one conventional cable or wire conductor lead design, individual, separately insulated conductors each occupy a separate lumen. In another design, multiple cable or wire conductors, each separately insulated, share a single lumen. In the first design, the number of cable or wire conductors that can be used is limited by the cross sectional area limitations of the lead body. In the second design, although multiple cable or wire conductors within a common lumen can allow for a smaller diameter lead, this design often entails inefficient, time-consuming individual conductor preparation and lead assembly, and may result in conductors being crossed during assembly.

Accordingly, despite significant advances made in the art, some of which have been summarized above, there continues to be a need for simpler, lower cost, smaller diameter, lead designs amenable to more efficient and reliable fabrication.

SUMMARY

In accordance with one exemplary embodiment, there is provided an implantable lead for transmitting electrical signals between a proximal end and a distal end of the lead, the lead comprising an elongated lead body defining a longitudinally-extending lumen, and a plurality of individual electrical conductors contained in the lumen of the lead body and extending between the proximal and distal ends, the plurality of individual conductors sharing a common insulating coating. Preferably, each of the plurality of individual electrical conductors may comprise a multifilar cable conductor of, for example, MP35N or MP35N/Ag alloy for superior flexibility and fatigue life. Alternatively, each of the plurality of individual electrical conductors may comprise a non-coiled monofilament wire of, for example, nitinol or MP35N.

According to one specific form of the invention, the common insulating coating electrically isolates the plurality of conductors from each other and may include a bridging portion extending between the individual conductors. The bridging portion of the common insulating coating may be perforated to impart additional flexibility to the coating.

According to another specific form of the invention, the conductors may be placed in electrical contact with each other along their lengths within the insulating coating. Such a configuration has a higher current-carrying capacity.

Pursuant to another aspect of the present invention, the plurality of electrical conductors and the common insulating coating comprise a conductor assembly. The conductor assembly in accordance with one form thereof may have a helical configuration defining a longitudinally-extending passageway for receiving a stylet, guide wire or the like for placing the distal end of the lead within the heart. In this helical configuration of the conductor assembly, the common insulating coating preferably has, in cross section, a generally oval shape with its longer dimension extending in the longitudinal direction. The plurality of individual conductors are preferably spaced apart in the longitudinal direction within the generally oval shaped common insulating coating to minimize the outer dimension of the lead body.

Pursuant to another form thereof, the conductor assembly may have a tubular configuration. The plurality of individual conductors is embedded within the common insulating coating of the tubular conductor assembly and may be arranged in spaced-apart, parallel relationship. Alternatively, the embedded plurality of conductors may follow a generally helical path along the length of the lead body for greater lead body flexibility.

The lead of the present invention provides a robust structure while reducing the number of components thereby simplifying the lead structure and decreasing manufacturing costs. The jointly coated, multiple conductor assemblies of the invention are more easily handled during production; for example, they can be threaded in a single operation and eliminate the problem of crossing conductors during assembly. Further, the multiple conductors of a jointly coated conductor assembly may be ablated in a single operation instead of the current time-consuming method of separately ablating each individually coated conductor.

BRIEF DESCRIPTION OF THE DRAWINGS

The foregoing and other objects, features and advantages of the invention will be evident to those skilled in the art from the detailed description of the invention, below, taken together with the accompanying drawings, in which:

FIG. 1 is a side view of an endocardial pacing, sensing and defibrillation lead in accordance with one embodiment of the present invention;

FIG. 2 is a transverse cross section view of the lead shown in FIG. 1, as seen along the line 2—2 in FIG. 1;

FIG. 3 is a transverse cross section view of a lead in accordance with an alternative embodiment of the present invention;

DETAILED DESCRIPTION OF THE INVENTION

Figure 4:
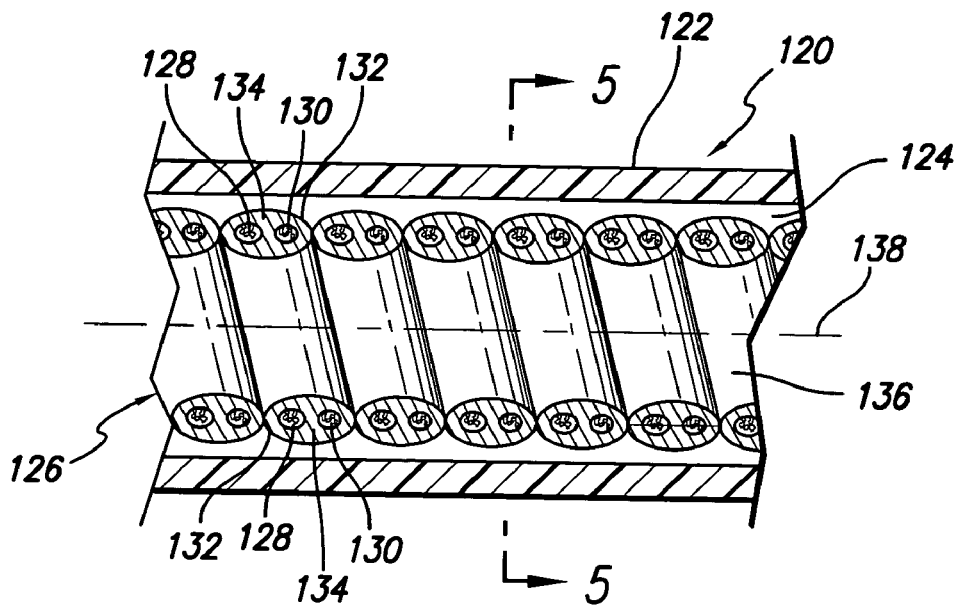
FIG. 4 is an axial cross section view of a portion of a lead pursuant to another, alternative embodiment of the present invention.

The following description presents preferred embodiments of the invention representing the best mode contemplated for practicing the invention. This description is not to be taken in a limiting sense but is made merely for the purpose of describing the general principles of the invention whose scope is defined by the appended claims.

FIG. 1 shows an endocardial pacing, sensing and defibrillation lead 10 including a lead body 12 having a proximal end 14 and a distal end 16. The lead 10 is illustrated to be of a bipolar design, but is not intended to be limiting of the invention. The proximal end 14 of the lead incorporates a connector assembly 18 compatible with a standard such as the IS-1 standard for connecting the lead body 12 to an implantable medical device in the form of a pacemaker/ICD 20. The connector assembly 18 includes a tubular pin terminal contact 22 and ring terminal contacts 23 and 24 electrically coupled to electrodes along the distal end of the lead body. The connector assembly 18 of the lead is received within a receptacle in the medical device 20 containing electrical contacts positioned to engage the contacts 22–24 on the connector assembly 18. As is well known in the art, to prevent ingress of body fluids into the receptacle, the connector assembly is provided with spaced sets of seals 26. In accordance with standard implantation techniques, a stylet or guide wire (not shown) for delivering and steering the distal end 16 of the lead body 12 during implantation is inserted into a lumen of the lead body through the tubular connector terminal pin 22.

The lead body 12 extends along a central, longitudinal axis 28 and preferably comprises a tubular sheath or housing 30 made of an insulating, biocompatible, biostable polymer, for example, silicone rubber or polyurethane.

The distal end 16 of the lead body 12 may carry one or more electrodes whose configurations, functions and placement along the length of the distal portion will be dictated by the indicated stimulation therapy, the peculiarities of the patient's anatomy, and so forth. The lead shown in FIG. 1 illustrates but one example of the various combinations of stimulating and/or sensing electrodes that may be utilized. More particularly, the distal end 16 of the lead body 12 terminates at a distal extremity 32 incorporating an electrical stimulating and/or sensing tip electrode 34 having an outer surface 36. As is well known in the art, the distal end 16 of the lead body 12 is placed so as to position the surface 36 of the tip electrode 34 in electrical communication with the body tissue to be stimulated and/or sensed.

Disposed along the distal end 16 of the lead body 12 proximally of the tip electrode 34 are passive fixation means that may take the form of conventional tines 40 for anchoring the lead body within the right atrium or right ventricle of the heart. Alternatively, the passive fixation or anchoring means may comprise one or more preformed humps, spirals, S-shaped bends, or other configurations (not shown) manufactured into the distal end 16 of the lead body where the lead is intended for left heart placement within a vessel of the coronary sinus region. The fixation means may also comprise an active fixation mechanism such as a helix. It will be evident to those skilled in the art that any combination of the foregoing fixation or anchoring means can be employed.

The distal end 16 of the lead body 12 also carries a ring electrode 42 and a cardioverting or defibrillating coil 43. Although the ring electrode 42 may serve as both a tissue-stimulating and sensing electrode, it typically provides only a sensing function. The ring electrode 42 includes an outer surface 44 adapted to contact or otherwise electrically communicate with the body tissue to be stimulated and/or sensed. Other electrode configurations may, of course, be employed pursuant to lead constructions well known in the art. For example, an alternative electrode arrangement may include additional ring stimulation and/or sensing electrodes as well as additional cardioverting and/or defibrillating coils spaced apart along the distal end of the lead body.

As already indicated, FIG. 1 is illustrative only; the distal end 14 of the lead body may carry only pacing and sensing electrodes, only cardioverting/defibrillating electrodes or a combination of pacing, sensing and cardioverting/defibrillating electrodes. Where defibrillating electrodes are included these may be of conventional coil design or, for greater flexibility, they may comprise spaced apart, relatively short metallic rings or may be made of an electrically conductive polymer or coating. The kind of electrode configuration used will depend upon the particular application and accordingly any electrode configuration known in the art or developed in the future may be utilized. The various electrodes are connected to the terminal contacts 22–24 by way of electrical conductors, including conductor assemblies, arranged and constructed in accordance with the present invention.

In accordance with one form of the lead of the invention, the lead body may be isodiametric, that is, the outside diameter of the lead body may be the same throughout its entire length. By way of example and not limitation, the outside diameter of the lead body may range from about 0.026 inch (2 F) to about 0.130 inch (10 F). Also, in accordance with well known techniques, the outer surface of the lead body may have a lubricious coating along its length to facilitate its movement through a lead delivery introducer and the patient's vascular system.

Although the lead body may have various cross-sectional configurations, in accordance with a preferred embodiment of the invention, the lead body comprises a tubular, multi-lumen housing.

As noted, the electrode arrangement shown in FIG. 1 is illustrative only, and the lead body cross section shown in FIG. 2 is applicable to an embodiment of the lead 10 employing, besides a tip electrode, multiple ring and/or cardioverting/defibrillating electrodes. The lead body housing 30 is a quadrilumen structure defining four axially or longitudinally extending, parallel passages or lumens comprising a central lumen 50 and three outer lumens 52–54, arcuate in cross section, disposed about the central lumen 50. The central lumen may enclose a low friction liner 56 of PTFE, for example, through which a stylet, guide wire, or inner coil conductor may be passed for delivering and steering the distal of the lead body during implantation thereof.

Each of the lumens 52–54 contains a plurality of side-by-side, parallel, electrical conductors each preferably in the form of a multifilar, braided cable typically of MP35N or MP35N/Ag alloy. Alternatively, one or more of the plurality of conductors may each comprise a monofilament, non-coiled wire of, for example, nitinol, MP35N, or the like. The cable or wire conductors connect the various electrodes on the distal end of the lead body with associated terminal contacts on the proximal connector assembly. Alternatively, two or more of the conductors may be ganged, that is, connected in parallel, to supply a single electrode where greater electrical stimulation current is required.

In accordance with the invention, at least two of the plurality of conductors in each lumen share a common insulating cover, jacket or coating of ETFE or the like, the coating serving to facilitate lead fabrication and, in accordance with one form of the invention, to electrically isolate the commonly-coated conductors from each other. The insulating coatings may be applied using conventional techniques including extrusion, coextrusion, spraying and dipping (flood coating).

More specifically, the lumen 52 contains a pair of conductor assemblies 58 and 60. Since the assemblies 58 and 60 are identical, only the assembly 58 will be described in detail. The assembly 58 comprises a pair of parallel cable or wire conductors 62 and 64 sharing a common polymer insulating coating 66. The coating 66 includes a bridging portion 68 interposed between the conductors 62 and 64 for electrically isolating the spaced apart conductors. The length of the bridging portion 68 determines the flexibility of the conductor assembly 58 and hence that of the lead 10; the longer the bridging portion, the more flexible the conductor assembly.

The lumen 53 contains a conductor assembly 80 comprising a pair of electrical cable or wire conductors 82 and 84 jointly coated with a common insulating coating 86 having an electrically isolating bridge portion 88 interposed between the conductors. For greater lead flexibility, the bridging portion 88 is elongated. The flexibility of the lead may be further enhanced by forming longitudinally spaced-apart apertures 90 through the bridging portion 88. Instead of apertures, the bridging portion may have spaced apart notches, cuts or the like.

The lumen 54 contains a pair of conductor assemblies 96 and 98. The assembly 96 comprises a pair of electrical cable or wire conductors 100 and 102 jointly coated with a common insulating coating 104. In this case, however, the coating 104 does not have a bridging portion so that the conductors 100 and 102 are in electrical communication with each other along a longitudinal contact line 106. This arrangement has the advantage of permitting the conductor assembly 96 to carry greater current. Since the conductor assembly 98 is identical to the assembly 96, the assembly 98 need not be described in detail.

It will be evident that a lead body housing having one or more lumens may be employed, within the limitations of the lead body's cross sectional area, with each lumen containing one or more of any of the conductor assemblies described above. Moreover, it will be appreciated that each conductor assembly may comprise more than two cable or wire conductors sharing a common insulating coating.

FIG. 3 shows, in cross section, an alternative embodiment of the invention comprising a lead body 100 formed of a tubular, insulating sheath or housing 102 having a central lumen 104. The lumen 104 contains an inner, generally tubular structure 106 of insulating material such as ETFE or PTFE having embedded therein a plurality of parallel, longitudinally-extending non-coiled, monofilament wire conductors or braided, multifilar cable conductors or a combination of such conductors. As before, braided, multifilar cable conductors are preferred. In this example, eight electrical conductors 108–115 spaced apart circumferentially are employed. The conductors 108–115 electrically connect various electrodes disposed along the distal end of the lead body with terminal contacts on a proximal connector assembly (not shown). The inner tubular structure 106 defines a central lumen 116 providing access for a stylet or guide wire. Since the tubular structure is itself made of a low friction material, a low friction liner within the lumen 116 may be omitted. The lumen 116 may also contain an elongated coil having at its distal extremity a fixation helix, electrically active or inactive, whose extension is facilitated by the low friction properties of the structure 106.

All of the conductors 108–115 thus share a common insulating coating in the form of the tubular structure 106, with a bridging portion, such as the bridging portion 118, interposed between the individual, adjacent conductors. Each conductor may electrically connect a single electrode with a single, corresponding contact on the connector assembly; alternatively, two or more conductors may be connected in parallel, that is, ganged, for redundancy and/or greater current-carrying capacity. For this purpose, an adjacent pair of conductors may be in electrical contact along their lengths as already described in connection with the assemblies 96 and 98 in FIG. 2. It will be evident that although eight cable conductors 108–115 are shown, any number may be used. Further, it will be apparent that for increased lead flexibility, the conductors may follow helical paths within the tubular structure 106 along the length of the lead body 100.

Figure 5:
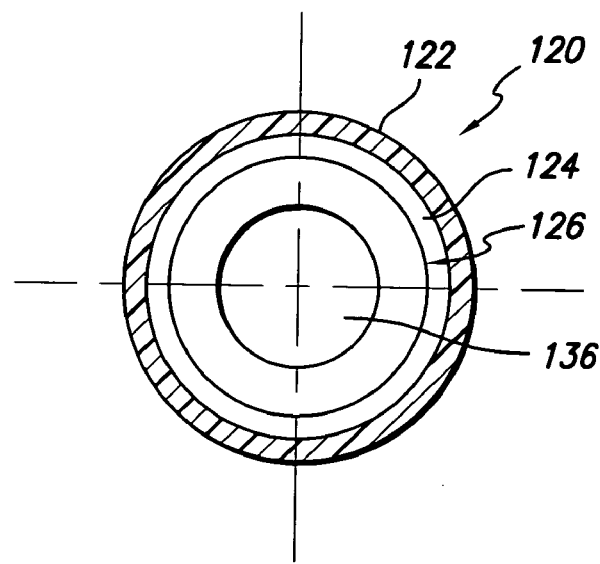
FIG. 5 is a transverse cross section of the portion of the lead shown in FIG. 4, as seen along the line 5—5 in FIG. 4.

FIGS. 4 and 5 show yet another embodiment of the invention comprising a lead body 120 having a tubular sheath or housing 122 of silicone rubber, polyurethane, or the like, defining a lumen 124. The lumen 124 contains an electrical conductor assembly 126 comprising a pair of conductors 128 and 130 in the form of either monofilament wire conductors or braided, multifilar cable conductors sharing a common insulating coating 132 of ETFE or the like electrically isolating the conductors from each other by means of a bridging portion 134. The conductor assembly 126 is wound in the form of a helical structure of constant diameter along the length of the assembly to enhance the flexibility of the lead. The conductors 128 and 130 are spaced apart within the insulating coating 132 in the longitudinal direction. Further in this regard, the cross section of the insulating coating 132 is preferably flattened, for example, in the general shape of an oval or ellipse, having its larger dimension extending in a longitudinal direction and its smaller dimension disposed transversely, that is, generally perpendicular to the longitudinal direction of the lead body. In this way, the outer diameter of the lead body 120 is minimized. The helical conductor assembly 126 defines an inner lumen or passageway 136 centered on a longitudinal axis 138 of the lead body. The inner passageway 136 may serve as a conduit for a lead-delivering and positioning stylet and/or guide wire. The passageway 136 may also contain an elongated coil having at its distal extremity a fixation helix, electrically active or inactive, whose extension is facilitated by the low friction properties of the insulating coating 132.

The ETFE coating is itself a low friction material so that a low friction liner within the inner passageway 136 may be omitted, thereby helping to minimize the outer diameter of the lead body.

While several illustrative embodiments of the invention have been shown and described, numerous variations and alternate embodiments will occur to those skilled in the art.

Such variations and alternate embodiments are contemplated, and can be made without departing from the spirit and scope of the invention as defined in the appended claims.

What is claimed is:

1. An implantable lead for transmitting electrical signals between a proximal end and a distal end, the lead comprising:
   a lead body defining at least one longitudinally-extending lumen; and
   a plurality of individual electrical conductors contained in the lumen of the lead body and extending between the proximal and distal ends, the plurality of individual conductors sharing a common insulating coating that insulates the plurality of individual conductors from each other, and each of the plurality of individual conductors comprise a same electrically conductive material;
   wherein the common insulating coating includes a bridging portion extending between individual conductors; and
   wherein the bridging portion of the common insulating coating is perforated to impart additional flexibility to the coating.

2. The lead of claim 1 in which:
   the plurality of electrical conductors and the common insulating coating comprise a conductor assembly.

3. The lead of claim 2 in which:
   the conductor assembly has a tubular configuration.

4. The lead of claim 3 in which:
   the plurality of individual conductors are embedded within the common insulating coating in spaced-apart, parallel relationship.

5. An implantable lead for transmitting electrical signals between a multiple-contact electrical connector at a proximal end of the lead and a plurality of electrodes disposed along a distal end of the lead, the electrical connector being adapted to be received by a receptacle in an implantable medical device, the lead comprising:
   a longitudinally-extending lead body comprising an insulating housing defining a plurality of longitudinally-extending lumens, at least one of the lumens containing an electrical conductor assembly comprising at least two electrical multifilar cable conductors sharing a common insulating coating, wherein the common insulating coating insulates the at least two electrical cable conductors from each other, the electrical cable conductors connecting at least one of the contacts on the electrical connector with at least one of the electrodes, and the at least two electrical cable conductors comprising a same electrically conductive material;
   wherein the common insulating coating electrically isolates the at least two cable conductors from each other, a first of the at least two cable conductors electrically connecting a first contact on the electrical connector with a first one of the plurality of electrodes, and a second of the at least two cable conductors electrically connecting a second contact on the electrical connector with a second one of the plurality of electrodes;
   wherein the common insulating coating includes a bridging portion extending between adjacent ones of the at least two electrical cable conductors; and
   wherein the bridging portion of the common insulating coating is perforated to impart additional flexibility to the coating.

6. The lead of claim 5 in which:
   each of at least two of the lumens contain an electrical conductor assembly, each of the conductor assemblies comprising at least two electrical multifilar cable conductors sharing a common insulating coating, the cable conductors of one of the conductor assemblies connecting at least one of the contacts on the electrical connector with at least one of the electrodes, and the cable conductors of the other of the conductor assemblies connecting at least one of the remaining contacts on the electrical connector with at least one of the remaining electrodes.

* * * * *